United States Patent [19]

Wong

[11] 4,210,496
[45] Jul. 1, 1980

[54] DISTILLATION PROCESS FOR RECOVERY OF HEXAMETHYL DISILOXANE

[75] Inventor: Wang-Mo Wong, Matteson, Ill.

[73] Assignee: Arthur G. McKee & Company, Independence, Ohio

[21] Appl. No.: 913,531

[22] Filed: Jun. 7, 1978

[51] Int. Cl.² .......................... B01D 3/36; C07F 7/20
[52] U.S. Cl. ...................................... 203/46; 203/44; 203/58; 203/63; 203/69; 556/456
[58] Field of Search .................... 203/44, 46, 50–70; 260/448.2 E

[56] References Cited

U.S. PATENT DOCUMENTS

| | | | |
|---|---|---|---|
| 2,439,777 | 4/1948 | Lake et al. | 203/58 |
| 3,803,195 | 4/1974 | Nitzsche et al. | 260/448.2 E |

FOREIGN PATENT DOCUMENTS 185922  10/1966  U.S.S.R. ............................ 260/448.2 E

Primary Examiner—Wilbur L. Bascomb, Jr.
Attorney, Agent, or Firm—Pearne, Gordon, Sessions, McCoy & Granger

[57] ABSTRACT

There is disclosed an azeotropic distillation process for separating and recovering hexamethyl disiloxane (HMDO) from toluene in a spent liquor mixture. An HMDO azeotrope former, pyrrolidone, is added to the liquor. The pyrrolidine is added in an amount of at least about 1.81 parts by weight per 1.0 part by weight of HMDO. Preferably, it is added in excess, as about 2.7 to about 5.4 parts by weight of pyrrolidine per 1.0 part by weight of HMDO. The resulting azeotrope of HMDO and pyrrolidine is then separated by distillation from the liquor. The pyrrolidine may be subsequently recovered from the HMDO by extraction with water. Other HMDO azeotrope formers, such as tertiary butanol, may also be utilized.

16 Claims, 1 Drawing Figure ically about 20 to 25 theoretical plates in the column and an overhead reflux ratio of about 10 to 20, a good overhead separation of at least 95% by weight HMDO is feasible.

DISTILLATION PROCESS FOR RECOVERY OF HEXAMETHYL DISILOXANE

DISCLOSURE OF THE INVENTION

1. Field of the Invention

This invention relates to a process for separating and recovering organic liquids in a spent liquor mixture. More particularly, this invention relates to an azeotropic distillation process for separating from toluene hexamethyl disiloxane, $(CH_3)_3SiOSi(CH_3)_3$, hereafter for convenience referred to as HMDO.

2. Background of the Invention

The separation of hexamethyl disiloxane (HMDO) from toluene is difficult because the vapor-liquid equilibrium is very close. Thus, fractionation of a by weight mixture of 92% toluene and 8% HMDO in a column of 40 to 50 theoretical plates at high reflux can achieve a recovery of no more than about 85% of HMDO by weight in the resulting overhead. It is apparent that essentially complete separation of HMDO from toluene by simple distillation is not feasible.

SUMMARY OF THE INVENTION

It is an object of the invention to overcome prior problems and provide an effective and commercially advantageous process of separating HMDO from toluene.

The invention provides a distillation process for separating a mixture of HMDO and toluene which comprises adding an HMDO azeotrope former to the mixture prior to distillation and then distilling the mixture to separate and recover a first fraction of the toluene and a second fraction of an azeotrope of the former and HMDO.

Preferably, this process is one wherein the azeotrope former is pyrrolidine and there is formed an azeotrope of HMDO and pyrrolidine.

Also preferably, the process is one wherein the pyrrolidine is added to the spent liquor mixture in an amount at least sufficient to form an azeotrope with all of the HMDO present in the mixture.

DESCRIPTION OF THE DRAWING

These and other aspects of the invention will be apparent from the following disclosure of a preferred process embodying the invention in connection with the accompanying drawing, in which.

DISCLOSURE OF A PREFERRED EMBODIMENT

Figure 1:
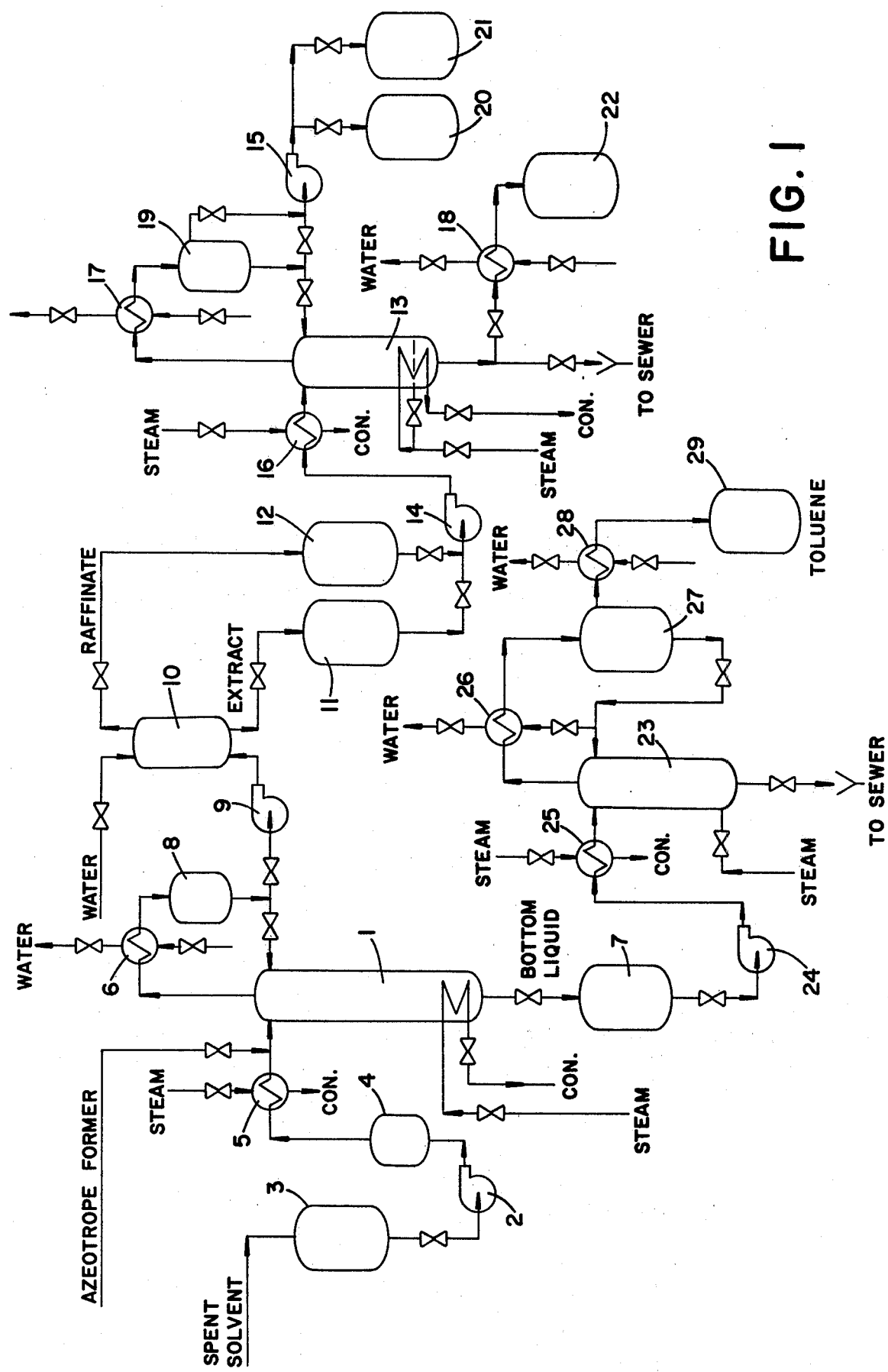
FIG. 1 of the drawing represents a schematic flow diagram of a distillation and extraction process utilized in the practice of this invention.

According to a preferred process of the present invention, hexamethyl disiloxane (HMDO) is separated from a mixture of HMDO and toluene by using pyrrolidine as an azeotrope former for the HMDO. For spent solvent containing essentially 91% by weight toluene, 8% by weight HMDO, and 1% by weight water, the solvent is first dehydrated with a suitable drying agent such as calcium oxide, sodium sulfate, silica gel, etc. The dry solvent is then fed into a distillation column with approximately 22 parts by weight of pyrrolidine per 99 parts by weight dry solvent. HMDO-pyrrolidine azeotrope along with excess pyrrolidine and any low boiling materials that may be present distill off as overhead at a temperature below approximately 88° C. The boiling temperature difference between the azeotrope and the toluene is at least approximately 22° C. This temperature difference causes the azeotrope to separate readily from the toluene. The overhead is condensed and a portion thereof is returned to the column as reflux while the remaining portion goes to a surge tank for further processing as described hereinafter. With the proper process distillation column design and operation, specifically about 20 to 25 theoretical plates in the column and an overhead reflux ratio of about 10 to 20, a good overhead separation of at least 95% by weight HMDO is feasible.

The toluene is withdrawn from the column as part of the bottom stream. Pure toluene is subsequently recovered from the bottom stream as overhead in a steam distillation process. The residue left in the bottom of the steam distillation goes to waste.

HMDO is recovered from the azeotrope by extraction with water. Because HMDO is insoluble in water while pyrrolidine is very soluble, pyrrolidine will go to the water phase. Pure HMDO is recovered by distilling the raffinate while pyrrolidine is recovered by the same process from the extract.

The pyrrolidine is added to the spent liquor mixture in an amount sufficient to form an azeotrope with all of the HMDO in the mixture, at least about 1.81 parts by weight pyrrolidine per 1.0 part by weight HMDO. In practice, the pyrrolidine is added in excess of the required azeotrope-forming amount with both the excess pyrrolidine and the azeotrope being recovered together as the distillation overhead fraction. Preferably the pyrrolidine is added in an excess amount of approximately 2.7 to about 5.4 parts by weight pyrrolidine per 1.0 part by weight HMDO.

The following example, discussed with specific reference to the process flow diagram in the drawing, represents the best embodiment known to and contemplated by the inventor in the practice of this invention. This example and embodiment illustrates the invention in terms of a continuous azeotropic distillation and extraction process.

EXAMPLE

Spent solvent, from a chemical process, containing 8% by weight HMDO, 1% by weight water, and 91% by weight toluene and a trace of non-volatile organic material, is used as feed. It is fed into a rectifying column 1 of approximately 20 theoretical plates by pump 2 from tank 3 through a dryer 4 and a heater 5. The dryer 4 is packed with a dehydrating agent, such as a silica gel, which is used to remove water from the feed. The resulting liquor is allowed to preheat to about 95° to 100° C. with steam before it flows to column 1. At the inlet to column 1, a stream of azeotrope former, pyrrolidine, is added to the liquor at a rate of about 22 parts by weight per 99 parts by weight of dry feed. An overhead, containing an azeotrope mixture of 35.6% by weight HMDO and 64.4% by weight pyrrolidine and an excess of pyrrolidine and some low boiling materials distills off from column 1 and passes to condenser 6. The bottom liquid, containing toluene and impurities, drops into tank 7.

After the overhead vapor has been condensed by condenser 6, the condensate drops into tank 8. Part of the condensate return to the rectifying column 1 as reflux at a reflux ratio of about 10 to 20. The remainder of the condensate is sent by pump 9 to the bottom of the extraction column 10. Individual solvent is isolated within the column by countercurrent extraction with water introduced at the top of column 10 in the proportion by weight of about 100 parts of water to 100 parts of condensate fed into column 10. The lower stream, as extract containing pyrrolidine and water, goes to tank 11 while the upper stream, as raffinate containing HMDO, flows to tank 12.

The recovery of pure solvent from these streams, extract and raffinate, is done by fractional distillation with rectifying column 13 and auxiliary equipment including pumps 14 and 15, heat exchangers 16, 17 and 18 and tanks 19, 20, 31 and 22, by much the same procedure as already described, with the following changes. By means of heater 16, the preheated temperature is 85° C. for the extract stream and 100° C. for the raffinate stream. The column 13 is shorter, having approximately 15 theoretical plates. To recover pure HMDO from the raffinate, residual pyrrolidine distills off as azeotrope with HMDO which after condensation in heat exchange condenser 17, is stored in tank 20. The pure HMDO bottom from column 13 is collected in tank 22.

Similarly, pure pyrrolidine is recovered as overhead from the extract stream by distillation in the same column 13. This overhead, after condensation in condenser 17 is collected in tank 21. The water bottom from column 13 is sent to waste.

Toluene is recovered from the bottom liquid in tank 7 by azeotropic distillation in column 23 with live steam. The liquid stream is pumped from tank 7 by pump 24 preheated to 85° C. with steam heater 25. Overhead from column 23 containing an azeotrope of toluene and water, passes through condenser 26 where it is condensed by cooling water and drops into tank 27, forming two layers. The lower water-rich layer is returned to column 23 as reflux. The upper toluene rich layer, after further cooling in cooler 28 flows into storage tank 29. The column 23 bottom containing water and impurities is sent to waste.

Although this invention has been disclosed and illustrated in terms of using pyrrolidine as an HMDO azeotrope former, it is contemplated that other HMDO azeotrope formers may be used.

Thus, in another embodiment of this invention, tertiary butanol is used as the azeotrope former. The recovery of spent liquor by azeotropic distillation with the azeotrope former tertiary butanol is quite similar to the pyrrolidine illustration. In this embodiment, the azeotrope composition is approximately 38% by weight HMDO and 62% tertiary butanol.

The tertiary butanol is added to the spent liquor mixture in an amount sufficient to form an azeotrope with all of the HMDO in the mixture, at least about 20 parts of tertiary butanol per 1.0 part HMDO by weight. Preferably, the tertiary butanol is added in excess in an amount ranging from about 2.8 to 3.0 parts by weight per 1.0 parts by weight of HMDO.

Other process conditions for the embodiment utilizing tertiary butanol include preheating the spent liquor to a temperature of about 75° to 77° C. The reflux ratio is the same, about 15 to 20 for column 1, and also remains unchanged for columns 13 and 23 as noted. The tertiary butanol is isolated from water by azeotropic distillation using benzene as the entrainer. This procedure is similar to recovery of anhydrous ethanol from a water solution. The HMDO raffinate is preheated to about 95° C. Otherwise, the process conditions of the tertiary butanol embodiment are about the same as the embodiment using pyrrolidine.

Other modifications may be made in the invention without departing from the spirit of the invention as set forth in the appended claims.

What is claimed is:

1. In a distillation process for separating a mixture of hexamethyl disiloxane (HMDO) and toluene, the improvement which comprises adding pyrrolidine to the mixture prior to distillation to form an azeotrope of HMDO and pyrrolidine and then distilling the mixture to separate and recover one fraction of the toluene and another fraction of said azeotrope.

2. The process of claim 1 wherein the pyrrolidine is added to the spent liquor mixture in an amount at least sufficient to form an azeotrope with all of the HMDO present in the mixture.

3. The process of claim 2 wherein the pyrrolidine is added to the spent liquor mixture in an amount of about from 2.7 to about 5.4 parts by weight per 1.0 part by weight of HMDO.

4. The process of claim 3 wherein the pyrrolidine is added to the spent liquor mixture in excess of the amount sufficient to form an azeotrope with all of the HMDO present in the mixture.

5. The process of any of claims 1, 2, 3 or 4 wherein the pyrrolidine is separated and recovered from the HMDO-pyrrolidine azeotrope by extraction with water.

6. The process of claim 4 wherein all of the pyrrolidine, including the excess and the azeotrope amount, is recovered by extraction with water.

7. An azeotropic distillation process for separating a mixture of hexamethyl disiloxane (HMDO) and toluene, which process comprises adding pyrrolidine to the mixture in an amount at least sufficient to form an azeotrope with all of the HMDO present in the mixture and then distilling the mixture to separate the azeotrope and the toluene.

8. The process of claim 7 wherein the pyrrolidine is added to the mixture in an amount of from about 2.7 to about 5.4 parts by weight per 1.0 part by weight of HMDO.

9. The process of either of claims 7 or 8 wherein the pyrrolidine is separated and recovered from the HMDO-pyrrolidine azeotrope by extraction with water.

10. In a distillation process for separating a mixture of hexamethyl disiloxane (HMDO) and toluene, the improvement which comprises adding tertiary butanol to the mixture prior to distillation to form an azeotrope of HMDO and tertiary butanol and then distilling the mixture to a separate and recover one fraction of the toluene and another fraction of said azeotrope.

11. The process of claim 10 wherein the tertiary butanol is added to the spent liquor mixture in an amount at least sufficient to form an azeotrope with all of the HMDO present in the mixture.

12. The process of claim 10 wherein the tertiary butanol is added to the spent liquor mixture in an amount of from about 2.8 to about 3.0 parts by weight per 1.0 part by weight of HMDO.

13. The process of claim 10 wherein the tertiary butanol is added to the spent liquor mixture in excess of the amount sufficient to form an azeotrope with all of the HMDO present in the mixture.

14. The process of any of claims 10, 11, 12 or 13 wherein the tertiary butanol is separated and recovered from the HMDO-tertiary butanol azeotrope by extraction with water.

15. The process of claim 13 wherein all of the tertiary butanol including the excess and the azeotrope amount, is recovered by extraction with water.

16. The process of claim 14 wherein the tertiary butanol is isolated from the water by azeotropic distillation using benzene as the entrainer.

* * * * *

UNITED STATES PATENT AND TRADEMARK OFFICE
CERTIFICATE OF CORRECTION

PATENT NO. : 4,210,496
DATED : July 1, 1980
INVENTOR(S) : WANG-MO WONG

It is certified that error appears in the above—identified patent and that said Letters Patent is hereby corrected as shown below:

In Column 4, lines 19 and 20, "about from 2.7" should read ---from about 2.7---.

In Column 4, line 54, "to a separate" should read ---to separate---.

The following claims should be added:

---17. The process of claim 7 wherein at least about 1.81 part of pyrrolidine are added to the mixture per 1.0 part by weight of HMDO.

18. The process of claim 10 wherein at least about two parts of tertiary butanol are added to the mixture for each part by weight of HMDO and wherein the tertiary butanol is separated and recovered from the HMDO-tertiary butanol azeotrope by extraction with water.---

On the cover sheet "16 claims" should read -- 18 claims --.

Signed and Sealed this

Eighteenth Day of November 1980

[SEAL]

Attest:

SIDNEY A. DIAMOND

Attesting Officer

Commissioner of Patents and Trademarks